(12) United States Patent
Chen et al.

(10) Patent No.: US 10,352,872 B2
(45) Date of Patent: Jul. 16, 2019

(54) DAMAGE DETECTION APPARATUS FOR LOCK GATE SILL

(71) Applicant: HoHai University, Nanjing, Jiangsu (CN)

(72) Inventors: Da Chen, Jiangsu (CN); Baodong Lou, Jiangsu (CN); Shuitao Gu, Jiangsu (CN); Feng Ouyang, Jiangsu (CN); Xingguo Feng, Jiangsu (CN); Lijun Hou, Jiangsu (CN)

(73) Assignee: Hohai University, Nanjing (CN)

( * ) Notice: Subject to any disclaimer, the term of this patent is extended or adjusted under 35 U.S.C. 154(b) by 312 days.

(21) Appl. No.: 15/356,529

(22) Filed: Nov. 18, 2016

(65) Prior Publication Data

US 2018/0011030 A1 Jan. 11, 2018

(30) Foreign Application Priority Data

Jul. 7, 2016 (CN) .......................... 2016 1 05340314

(51) Int. Cl.
| | |
|---|---|
| G01N 21/88 | (2006.01) |
| G01N 21/01 | (2006.01) |
| G01N 21/95 | (2006.01) |
| E02B 7/20 | (2006.01) |
| G01N 21/954 | (2006.01) |

(52) U.S. Cl.
CPC ......... *G01N 21/8851* (2013.01); *G01N 21/01* (2013.01); *G01N 21/95* (2013.01); *E02B 7/20* (2013.01); *G01N 21/954* (2013.01)

(58) Field of Classification Search
None
See application file for complete search history.

*Primary Examiner* — Richard C Gurtowski
(74) *Attorney, Agent, or Firm* — Thomas | Horstemeyer, LLP

(57) ABSTRACT

The present invention discloses a damage detection apparatus for a lock gate sill, including a support, a water storage tank, a water inlet barrel, a filter device, a water pump, and a control device, wherein a barrier is vertically disposed at the bottom of the water storage tank, multiple water discharge pipes are vertically disposed in the barrier, upper ends of the water discharge pipes are communicated with the water storage tank, the water discharge pipes have different heights, lower ports of the water discharge pipes together compose a truncated conical cavity, a camera is disposed at the bottom of the water storage tank in a sealed manner, and a lens of the camera is located in an upper part of the truncated conical cavity. When it is desired to perform damage detection for the lock gate sill, muddy water is filtered by the filter device into clear water, and the clear water is pressurized by the water pump and then discharged from the water discharge pipes, such that the muddy water in the barrier is continuously diluted by clear water, the camera is in a shooting environment of clear water, and the lock gate sill is shot for detection at this time, whereby it is ensured that the taken picture has good definition, and thus the position of abrasion and the amount of abrasion of the lock gate sill can be clearly determined.

15 Claims, 3 Drawing Sheets

DAMAGE DETECTION APPARATUS FOR LOCK GATE SILL

CROSS-REFERENCE TO RELATED APPLICATIONS

This application claims benefit and priority to Chinese patent application No. 2016105340314, which was filed on Jul. 7, 2016; the contents of which are incorporated by reference herein in its entirety.

BACKGROUND OF THE INVENTION

Field of the Invention

The present invention relates to the technical field of detection of a lock gate sill, and more specifically to an apparatus for detecting the damage degree of an underwater lock gate sill by a photographing technique.

Description of Related Art

The "super draught" of a ship means that the draught depth of the ship exceeds the allowed maximum safety depth of a ship lock. The "super draught" is the most common and direct threat to the safety of a operation ship lock at present, because it easily causes damages to the ship lock and severely threatens the safety of the construction of a dam.

Therefore, it is especially important to detect the abrasion condition of a lock gate sill regularly. The commonly used detection methods are underwater photographing, ultrasonic detection and etc. However, only the position of abrasion can be detected using ultrasonic detection and it is difficult to know the specific condition of the abrasion. The underwater photographing detection can detect the position of abrasion and the amount of abrasion of a lock gate sill in an intuitive manner, but light transmittance and visibility are rather limited during photographing in muddy water, so that the taken pictures have poor definition, thereby affecting the detection result.

SUMMARY OF THE INVENTION

Technical Problem

The objective of this present invention is to provide a damage detection apparatus for a lock gate sill, to solve the technical problem in the prior art that light transmittance and visibility are so limited that the taken pictures have poor definition when the lock gate sill is shot for detection in muddy water.

Technical Solution

To solve the above technical problem, the present invention adopts the following technical solutions:

A damage detection apparatus for a lock gate sill, including:

a support, wherein rollers enabling the damage detection apparatus for the lock gate sill to move are disposed at a lower part of the support, and motors driving the rollers to rotate are disposed on the support.

a water storage tank, disposed on the support, wherein a barrier is vertically disposed at the bottom of the water storage tank, an upper end of the barrier is hermetically connected to the bottom of the water storage tank, a lower end of the barrier has an opening structure, multiple water discharge pipes with different height are vertically disposed in the barrier, upper ends of the water discharge pipes are communicated with the water storage tank, lower ports of the water discharge pipes together compose a truncated conical cavity, a camera is disposed at the bottom of the water storage tank in a sealed manner, a lens of the camera is located in an upper part of the truncated conical cavity and coaxially disposed with the truncated conical structure, and the lower end of the barrier is below the lower ends of the water discharge pipes.

a water inlet barrel, fixed above the water storage tank, wherein a cylindrical cavity is provided in the water inlet barrel, water inlet passages are provided in an upper end of the water inlet barrel, a filter device is disposed in the water inlet barrel, a sediment discharge pipe is disposed on the filter device for discharging sediment filtered out by the filter device, and a water outlet is provided at the lower end of the water inlet barrel. The lower ports of the water discharge pipes together compose the truncated conical cavity, the design of the truncated conical shape ensures that the lens of the camera has a wide range of the shooting angle and is not interfered with the lower ends of the water discharge pipes.

a water pump, disposed on the support, wherein the water inlet end of the water pump is communicated with the water outlet of the water inlet barrel, and the water outlet end of the water pump is communicated with the water storage tank;

a control device, disposed in a sealed manner on the support, wherein the camera, the motors and the control device are electrically interconnected.

a telecontrol device, electrically connected to the control device, wherein the telecontrol device is placed on the bank of a lock gate when damage detection is performed for the lock gate sill.

a display device, electrically connected to the control device, wherein the display device is placed on the lock gate bank when the damage detection is performed for the lock gate sill.

When it is desired to perform damage detection for the lock gate sill, the detection apparatus is placed underwater and on an upper surface of the lock gate sill, and by manipulating a button of the telecontrol device, the control device starts the motors, the water pump and the camera. The motors drive the rollers to rotate, and the detection apparatus is able to move forward. Meanwhile, muddy water enters the water inlet barrel from the water inlet passages and is filtered by the filter device, sediment is discharged via the sediment discharge pipe, clear water is pressurized by the water pump and then enters the water storage tank, and clear water in the water storage tank is discharged from the water discharge pipes. Because the pressure of the clear water discharged from the water discharge pipes is higher than that of the surrounding muddy water and the water discharge pipes keep discharging clear water, the muddy water in the barrier is continuously diluted by the clear water. Because the lower end of the barrier is below the lower ends of the water discharge pipes, the barrier is full of clear water after a while, so that the camera is in a shooting environment of clear water, and if the lock gate sill is shot for detection at this time, it is ensured that the taken pictures have very good definition, and thus the position of abrasion and the amount of abrasion of the lock gate sill can be clearly shown. The taken pictures are transmitted to the display device in time by means of the control device, such that the detection personnel on the lock gate bank can learn about the detection result in an intuitive manner. By disposing the telecontrol device, it is convenient for the detection personnel to manipulate the detection apparatus.

In a further improvement, the filter device comprises a first hopper, a support element is disposed in the water inlet barrel and is fixedly connected to the inner wall of the water inlet barrel, the bottom of the first hopper is connected to the support element, the first hopper is coaxially disposed with the water inlet barrel, an upper edge of the first hopper is hermetically connected to the inner wall of the water inlet barrel, several filter holes are set on the first hopper, and the neck of the first hopper is communicated with the sediment discharge pipe. When muddy water is filtered by the hopper, clear water falls from the filter holes, and sediment slides down along the inner wall of the hopper under the effect of gravity and enters the sediment discharge pipe.

In a further improvement, a lower part of the first hopper is rotatably connected to the support element by a bearing, the upper edge of the first hopper is hermetically and movably connected to the inner wall of the water inlet barrel, multiple baffle plates are disposed on an inner wall of the first hopper, the water inlet passages in the upper end of the water inlet barrel are obliquely provided, and water flows rush into the water inlet barrel from the oblique water inlet passages and impact on the baffle plates, thereby driving the first hopper to rotate. By obliquely disposing the water inlet passages, the water flows entering the water inlet barrel have specific directivity, and the water flows impact on the baffle plates to exert an oblique thrust on the baffle plates, such that the first hopper rotates and sediment is prevented from blocking the filter holes on the inner wall of the hopper.

In a further improvement, the baffle plates are evenly distributed on the inner wall of the first hopper and are all obliquely disposed in a clockwise or an anticlockwise direction, the tilt direction of the baffle plates is opposite to that of the water inlet passages. By disposing the baffle plates in the same direction, it is ensured that each baffle plate experiences the same centripetal force under the impact of the water flows, thereby enabling the hopper to rotate at a constant speed.

In a further improvement, the number of the water inlet passages is two, the two water inlet passages are radially disposed and have the same tilting direction. By increasing the number of the water inlet passages, the impact of the water flows on the baffle plates is increased, which raises the rotation speed of the hopper and accelerates falling of the sediment.

In a further improvement, the filter device further includes a second hopper, the second hopper is located below the first hopper, a connecting element is disposed on the second hopper, the second hopper is fixed to the neck of the first hopper by the connecting element, the neck of the second hopper is fixedly connected to an inner ring of the bearing, the neck of the second hopper is communicated with the sediment discharge pipe, the second hopper is coaxially disposed with the first hopper, the inner diameter of the neck of the second hopper is larger than the outer diameter of the neck of the first hopper, the neck of the first hopper is inserted in the neck of the second hopper, several small filter holes are provided on the second hopper, and the size of the small filter holes is smaller than that of the filter holes. By disposing the second hopper, the clear water obtained after filtering via the first hopper falls from the filter holes into the second hopper, the clear water obtained after filtering via the second hopper enters the water storage tank through the water pump, and the sediment enters the sediment discharge pipe. Because the size of the small filter holes is smaller than that of the filter holes, the filtering effect is improved, the light transmittance of the water environment for photographing is improved, and it is ensured that the taken picture is clearer. Because the inner diameter of the neck of the second hopper is larger than the outer diameter of the neck of the first hopper and the neck of the first hopper is inserted in the neck of the second hopper, sediment in both the first hopper and the second hopper is discharged from the sediment discharge pipe. Because the second hopper is fixed to the first hopper, after the water flows impact on the baffle plates, an oblique thrust is exerted on the baffle plates, and the first hopper and the second hopper rotate together, which accelerates falling of the sediment.

In a further improvement, four rollers are disposed at the lower part of the support, which are respectively driven by the four motors, thereby increasing the driving force of the detection apparatus.

In a further improvement, the four rollers are evenly divided into two sets, gears are disposed on each roller, and a track is sleeved on each set of two rollers. The disposing of the track increases the contact area between the whole detection apparatus and the upper surface of the lock gate sill, which improves the stability of detection, prevents the occurrence of overturn and the like, and ensures that the two rollers of each set rotate synchronously.

In a further improvement, the outlet position of the sediment discharge pipe is opposite to the forward direction of the damage detection apparatus for the lock gate sill, which prevents the sediment from falling in the forward direction of the detection apparatus to make water muddier and thus affect the detection result.

In a further improvement, an arc-shaped plate is disposed at a front end of the water storage tank, such that the front end of the detection apparatus is in a bow shape, which reduces the water resistance when the damage detection apparatus for the lock gate sill moves forward.

In a further improvement, the water storage tank has a regular octagonal prism structure, the water inlet barrel is cylindrical, and the water storage tank is coaxially disposed with the water inlet barrel, which ensures the center of gravity of the detection apparatus falls on an the same axis and thereby improves the stability.

In a further improvement, a battery pack is disposed on the support for supplying power to the control module, the motors and the camera. As such, no external cable is required to supply power to the detection apparatus and thus winding is prevented. Meanwhile, the battery pack may serve as a counterweight to increase the stability of the whole detection apparatus.

In a further improvement, the display device is connected to the control device by a cable, and the picture taken by the camera is transmitted through the cable to the display device.

In a further improvement, the display device electrically communicates with the control device by means of a wireless communication module, and the picture taken by the camera is transmitted in a wireless manner to the display device.

In a further improvement, a withdrawal rope is tied on the damage detection apparatus for the lock gate sill, and one end of the rope is placed on the lock gate bank when damage detection is performed. By disposing the rope, it is convenient to salvage and withdraw the detection apparatus after detecting.

Advantageous Effect

Compared with the prior art, the present invention has the following beneficial effects:

1. Muddy water is filtered by the filter device into clear water, and clear water is pressurized by the water pump and then discharged from the water discharge pipes, such that the muddy water in the barrier is continuously diluted by clear water, the camera is in a shooting environment of clear water, and the lock gate sill is shot for detection at this moment. It is ensured that the taken picture has good definition, and thus the position of abrasion and the amount of abrasion of the lock gate sill can be clearly shown.

2. The lower ports of the water discharge pipes together compose the truncated conical cavity, the design of the truncated conical shape ensures that the lens of the camera has a wide range of the shooting angle, and the lower ends of the water discharge pipes do not interfere with the lens of the camera.

3. When muddy water is filtered by the hopper, clear water falls from the filter holes, and sediment slides down along the inner wall of the hopper under the effect of gravity and enters the sediment discharge pipe. The water flows impact on the baffle plates and exert an oblique thrust on the baffle plates, such that the hopper rotates and sediment is prevented from blocking the filter holes on the inner wall of the hopper.

4. By disposing the multi-layer-hopper filter device, the filtering effect would be improved and the light transmittance of the shooting environment of the camera is further improved. It is ensured that the taken picture has good definition.

5. The disposing of the track increases the contact area between the whole detection apparatus and the upper surface of the lock gate sill, which improves the stability of detection, prevents the occurrence of overturn and the like, and ensures that the two rollers of each set rotate synchronously.

6. By disposing the remote control device, it is convenient for the detection personnel on the lock gate bank to control the detection apparatus.

7. By disposing the rope, it is convenient to salvage and withdraw the detection apparatus after detecting.

DETAILED DESCRIPTION OF THE INVENTION

To better understand the present invention, the content of the present invention is further illustrated below in connection with embodiments, but the content of the present invention is not only limited to the following embodiments.

Figure 1:
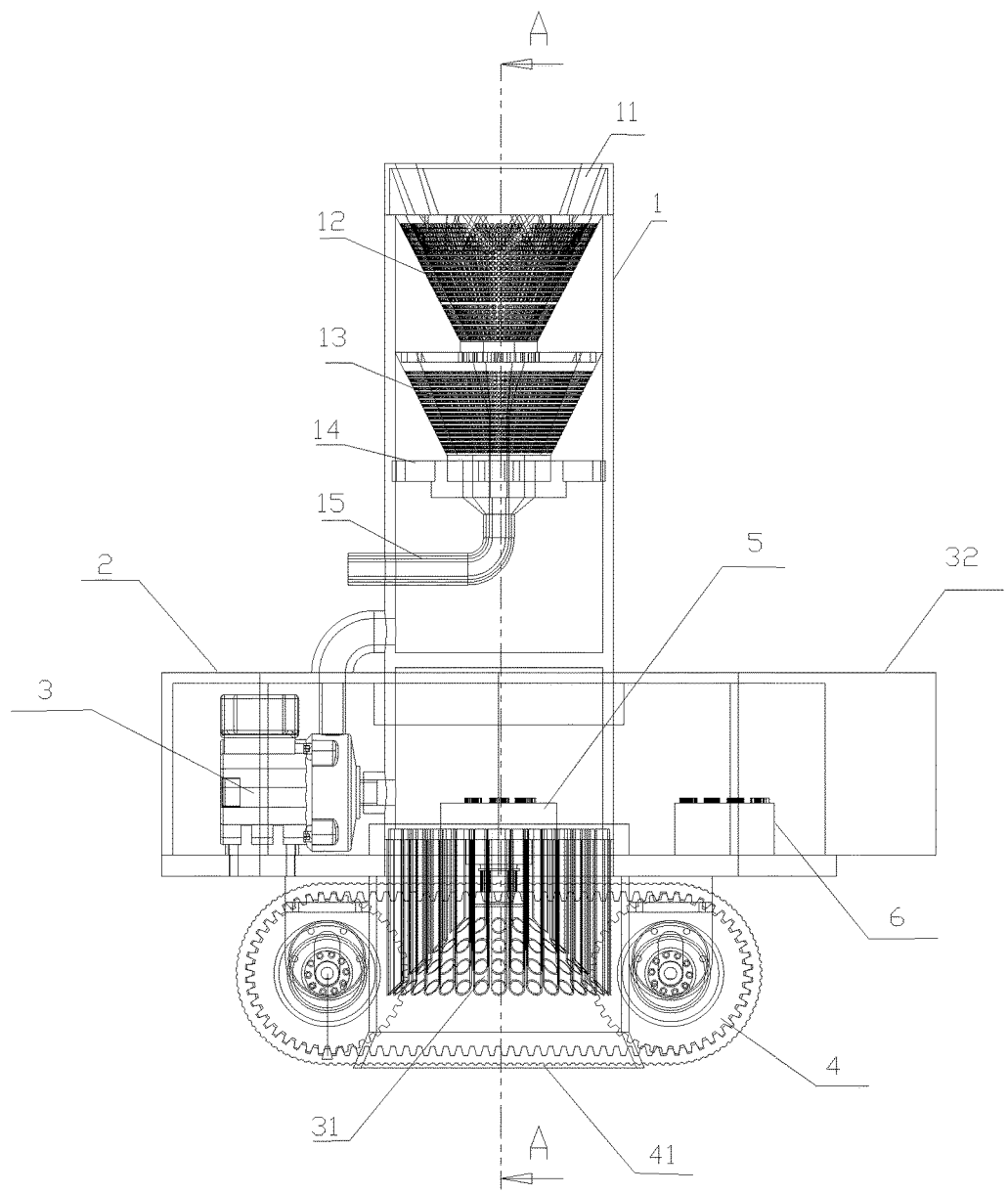
FIG. 1 is a structural diagram of a damage detection apparatus for a lock gate sill in the present invention.
Figure 2:
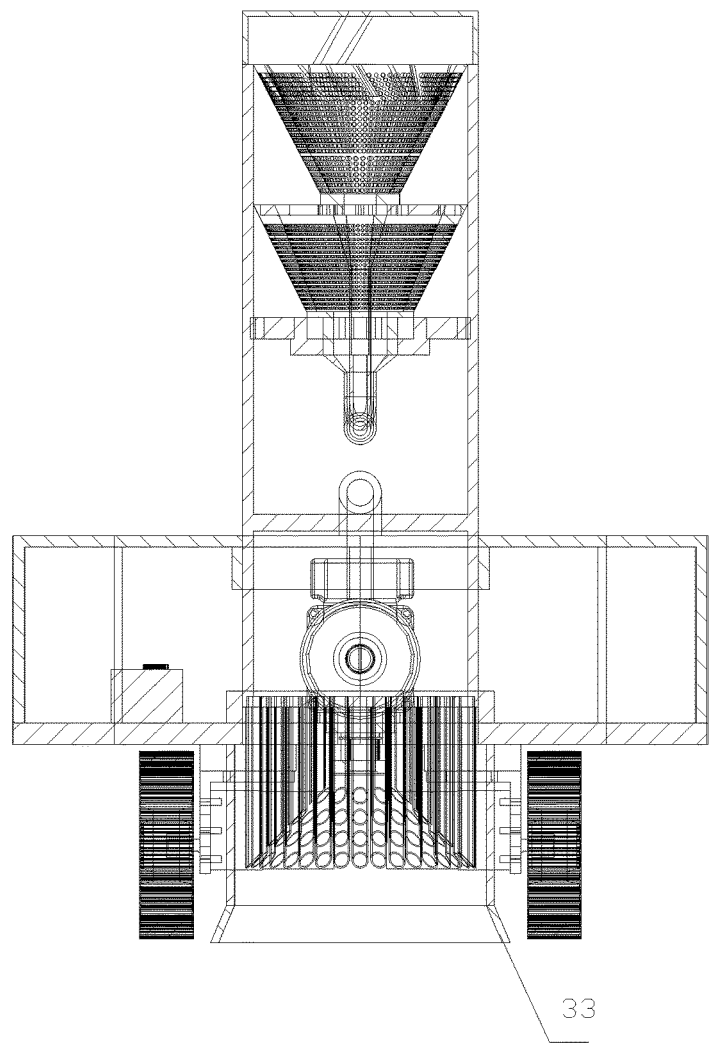
FIG. 2 is a cross-sectional diagram taken along a line A-A in FIG. 1.
Figure 3:
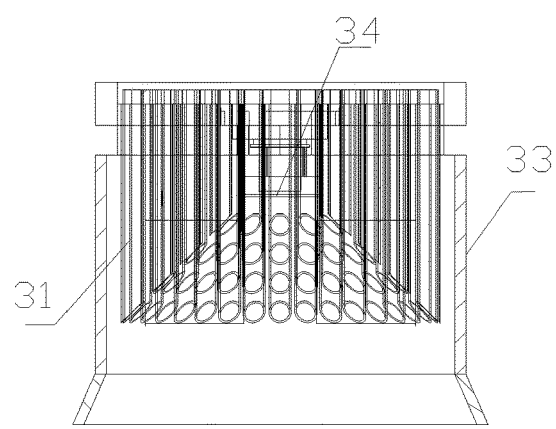
FIG. 3 is a combined structural diagram of a barrier, water discharge pipes and a camera.
Figure 4:
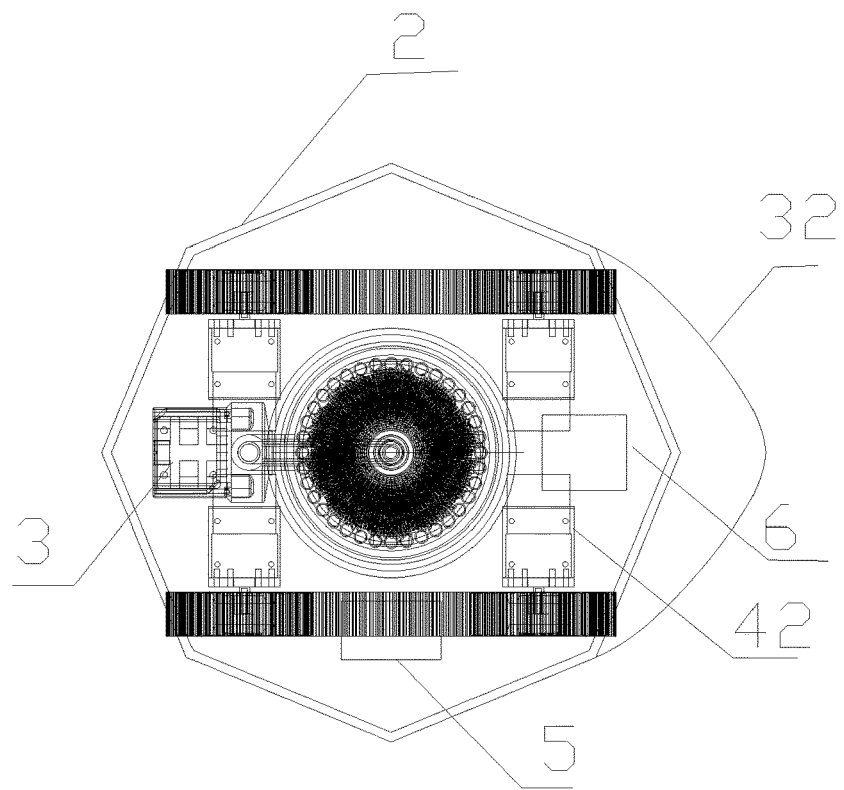
FIG. 4 is a top view of FIG. 1.
Figure 5:
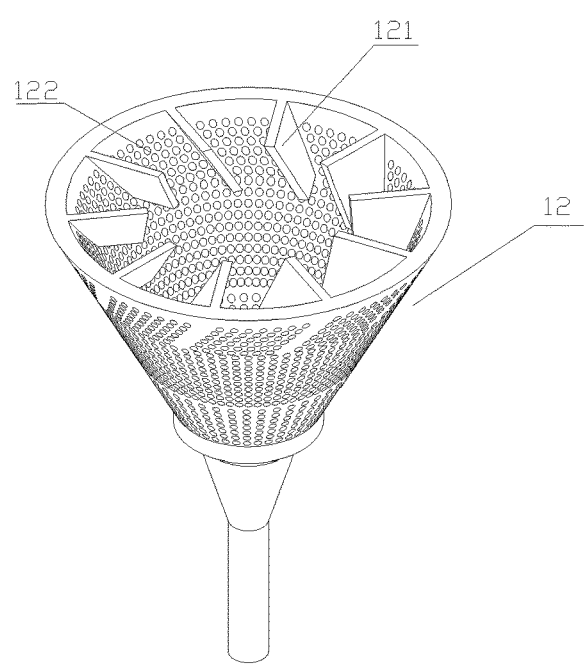
FIG. 5 is a structural diagram of a first hopper.

As shown in FIGS. 1-5, a damage detection apparatus for a lock gate sill covers technical features including a water inlet barrel 1, water inlet passages 11, a first hopper 12, baffle plates 121, filter holes 122, a second hopper 13, a support element 14, a sediment discharge pipe 15, a water storage tank 2, a water pump 3, water discharge pipes 31, an arc-shaped plate 32, a barrier 33, a camera 34, rollers 4, a track 41, motors 42, a battery pack 5, and a control module 6.

A damage detection apparatus for a lock gate sill, including:
a support, wherein rollers 4 enabling the damage detection apparatus for the lock gate sill to move are disposed at a lower part of the support, and motors 42 driving the rollers to rotate are disposed on the support;
a water storage tank, disposed on the support, wherein a barrier 33 is vertically disposed at the bottom of the water storage tank, an upper end of the barrier is hermetically connected to the bottom of the water storage tank 2, a lower end of the barrier has an opening structure, multiple water discharge pipes 31 are vertically disposed in the barrier, upper ends of the water discharge pipes are communicated with the water storage tank, the water discharge pipes have different heights, lower ports of the water discharge pipes together compose a truncated conical cavity, a camera 34 is disposed at the bottom of the water storage tank in a sealed manner, The lens of the camera is located in the upper part of the truncated conical cavity and coaxially disposed with the truncated conical cavity, and the lower end of the barrier is below the lower ends of the water discharge pipes 31;
a water inlet barrel 1, fixedly disposed above the water storage tank 2, wherein a cylindrical cavity is disposed in the water inlet barrel, water inlet passages 11 are provided in an upper end of the water inlet barrel, the water inlet passages are communicated with the cylindrical cavity, a filter device is disposed in the cylindrical cavity, a sediment discharge pipe 15 is disposed on the filter device for discharging sediment filtered out, and a water outlet is disposed at a lower end of the water inlet barrel;
a water pump 3, disposed on the support, wherein a water inlet end of the water pump is communicated with the water outlet of the water inlet barrel, and a water outlet end of the water pump is communicated with the water storage tank;
a control device, disposed on the support in a sealed manner, wherein the camera, the motors and the control device are electrically connected to each other;
a remote control device, electrically connected to the control device, wherein the remote control device is placed on the lock gate bank when damage detection is performed on the lock gate sill;
a display device, electrically connected to the control device, wherein the display device is placed on the lock gate bank when the damage detection is performed on the lock gate sill.

When it is desired to perform damage detection for the lock gate sill, the detection apparatus is placed underwater and on an upper surface of the lock gate sill, and by manipulating a button of the remote control device, the control device starts the motors, the water pump and the camera. The motors drive the rollers to rotate, and the detection apparatus is able to move forward. Meanwhile, muddy water enters the water inlet barrel from the water inlet passages and is filtered by the filter device, sediment is discharged via the sediment discharge pipe, clear water is pressurized by the water pump and then enters the water storage tank, and the clear water in the water storage tank is discharged from the water discharge pipes. Because the pressure of the clear water discharged from the water discharge pipes is higher than that of the surrounding muddy water and the water discharge pipes keep discharging clear water, the muddy water in the barrier is continuously diluted by the clear water. Because the lower end of the barrier is below the lower ends of the water discharge pipes, the barrier is full of clear water after a while, the camera is in a shooting environment of clear water, and if the lock gate sill is shot for detection at this time, it is ensured that the taken picture has good definition, and thus the position of abrasion and the amount of abrasion of the lock gate sill can be clearly shown. The taken picture is transmitted to the display device in time by means of the control device, such that detection personnel on the lock gate bank can learn about the detection result in an intuitive manner. By disposing the remote control device, it is convenient for the detection personnel to manipulate the detection apparatus.

In the present embodiment, the filter device includes a first hopper 12, a support element is disposed in the water inlet barrel and is fixedly connected to an inner wall of the water inlet barrel. The bottom of the first hopper is connected to the support member 14, the first hopper is coaxially disposed with the water inlet barrel 2, an upper edge of the first hopper is hermetically connected to the inner wall of the water inlet barrel, several filter holes 122 are set on the first hopper, and the neck of the first hopper is communicated with the sediment discharge pipe 15. When the muddy water is filtered using the hopper, clear water falls from the filter holes, and sediment slides down along the inner wall of the hopper under the effect of gravity and enters the sediment discharge pipe.

In the present embodiment, a lower part of the first hopper is rotatably connected to the support member by a bearing, the upper edge of the hopper is hermetically movably connected to the inner wall of the water inlet barrel, multiple baffle plates 121 are disposed on an inner wall of the first hopper, the water inlet passages in the upper end of the water inlet barrel are obliquely provided, and water flows rush into the water inlet barrel 2 from the oblique water inlet passages 11 and impact on the baffle plates, thereby driving the first hopper to rotate. By obliquely disposing the water inlet passages, the water flows entering the water inlet barrel have specific directivity, and the water flows impact on the baffle plates to exert an oblique thrust on the baffle plates, such that the first hopper rotates and sediment is prevented from being accumulated on the inner wall of the hopper to block the filter holes.

In the present embodiment, the baffle plates are evenly distributed on the inner wall of the first hopper and are all obliquely disposed in a clockwise or an anticlockwise direction, and the tilt direction of the baffle plates is opposite to that of the water inlet passages. By disposing the baffle plates in the same direction, it is ensured that each baffle plate experiences the same centripetal force under the impact of the water flows, thereby enabling the hopper to rotate at a constant speed.

In the present embodiment, the number of the water inlet passages is two, the two water inlet passages are radially disposed, and the tilt directions of the two water inlet passages are the same. By increasing the number of the water inlet passages, the impact of the water flows on the baffle plates is increased, which raises the rotation speed of the hopper and accelerates falling of the sediment.

In the present embodiment, the filter device further includes a second hopper, the second hopper is located below the first hopper, the neck of the first hopper is inserted in the neck of the second hopper, the inner diameter of the neck of the second hopper is larger than the outer diameter of the neck of the first hopper, the neck of the first hopper is fixed to the second hopper by means of a connecting member, the second hopper is coaxially disposed with the first hopper, the neck of the second hopper is rotatably connected to the support member by a bearing, the bottom of the neck of the second hopper is communicated with the sediment discharge pipe, several filter holes are set on the second hopper, and the size of the filter holes is smaller than that of the filter holes of the first hopper. By disposing the second hopper, the clear water obtained after filtering via the first hopper falls from the filter holes into the second hopper, the clear water obtained after filtering via the second hopper enters the water storage tank through the water pump, and the sediment enters the sediment discharge pipe. Because the size of the filter holes of the second hopper is smaller than that of the filter holes of the first hopper, the filtering effect is improved, and clearer water is obtained after filtering of the muddy water, such that the light transmittance of the water environment for photographing is improved, and it is ensured that the taken picture is clearer. Because the inner diameter of the neck of the second hopper is larger than the outer diameter of the neck of the first hopper and the neck of the first hopper is inserted in the neck of the second hopper, sediment in both the first hopper and the second hopper is discharged from the sediment discharge pipe. Because the second hopper is fixed to the first hopper, after the water flows impact on the baffle plates, an oblique thrust is exerted on the baffle plates, and the first hopper and the second hopper rotate together, which accelerates falling of the sediment.

More hoppers may be disposed in this manner for step-by-step filtering in the present application, thereby improving the filtering effect.

In the present embodiment, four rollers are disposed at the lower part of the support, and the four rollers are respectively driven by the four motors, thereby increasing the driving force of the detection apparatus.

In the present embodiment, the four rollers are evenly divided into two sets, gears are disposed on each roller, and a track 41 is sleeved on each set of two rollers. The disposing of the track increases the contact area between the whole detection apparatus and the upper surface of the lock gate sill, which improves the stability of detection, prevents the occurrence of overturn and the like, and ensures that the two rollers of each set rotate synchronously.

In the present embodiment, the outlet position of the sediment discharge pipe is opposite to the forward direction of the damage detection apparatus for the lock gate sill, which prevents the sediment discharged from the sediment discharge pipe from falling in the forward direction of the detection apparatus to make water muddier and thus affect the detection result.

In the present embodiment, an arc-shaped plate is disposed at a front end of the water storage tank, such that the front end of the detection apparatus is in a bow shape, which reduces the water resistance when the damage detection apparatus for the lock gate sill moves forward. The "front end" herein is defined relative to the forward direction of the detection apparatus.

In the present embodiment, the water storage tank has a regular octagonal prism structure, the water inlet barrel is cylindrical, and the water storage tank is coaxially disposed with the water inlet barrel, which ensures that the center of gravity of the detection apparatus falls on the same axis and thereby improves the stability.

In the present embodiment, a battery pack is disposed on the support for supplying power to the control module, the motors and the camera. In addition, no external cable is required to supply power to the detection apparatus and thus winding is prevented. Meanwhile, the battery pack may serve as a counterweight to increase the stability of the whole detection apparatus.

In the present embodiment, the display device electrically communicates with the control device by a wireless communication module, and the picture taken by the camera is transmitted in a wireless manner to the display device for display. In other embodiments, the display device is connected to the control device by a cable, and the picture taken by the camera is transmitted through the cable to the display device for display.

In the present embodiment, a withdrawal rope is tied on the damage detection apparatus for the lock gate sill, and one end of the rope is placed on the lock gate bank when damage detection is performed on the lock gate sill. By disposing the rope, it is convenient to salvage and withdraw the detection apparatus after the detection is finished.

Those not particularly described in the present invention all belong to the existing techniques or may be implemented by the existing techniques, and the specific embodiments in the present invention are merely preferred embodiments of the present invention, and are not intended to limit the implementation scope of the present invention. Any equivalent change and modification made in accordance with the content of the claims of the present invention shall fall within the technical scope of the present invention.

What is claimed is:

1. A damage detection apparatus for a lock gate sill, comprising:
   a) a support, wherein rollers enabling the damage detection apparatus for the lock gate sill to move are disposed at a lower part of the support, and wherein motors driving the rollers to rotate are disposed on the support;
   b) a water storage tank disposed on the support, wherein a barrier is vertically disposed at a bottom of the water storage tank, wherein an upper end of the barrier is hermetically connected to the bottom of the water storage tank, wherein a lower end of the barrier has an opening structure, wherein multiple water discharge pipes are vertically disposed in the barrier, wherein upper ends of the water discharge pipes are communicated with the water storage tank, wherein the water discharge pipes have different heights, wherein lower ports of the water discharge pipes together compose a truncated conical cavity, wherein a camera is disposed at the bottom of the water storage tank in a sealed manner, wherein a lens of the camera is located in an upper part of the truncated conical cavity and is coaxially disposed with the truncated conical cavity, and wherein the lower end of the barrier is below lower ends of the water discharge pipes;
   c) a water inlet barrel fixed above the water storage tank, wherein a cylindrical cavity is provided in the water inlet barrel, wherein water inlet passages are provided in an upper end of the water inlet barrel that are communicated with the cylindrical cavity, wherein a filter device is disposed in the water inlet barrel, wherein a sediment discharge pipe is connected to the filter device for discharging sediment filtered out by the filter device, and wherein a water outlet is provided at a lower end of the water inlet barrel;
   d) a water pump disposed on the support, wherein a water inlet end of the water pump is communicated with the water outlet of the water inlet barrel, and wherein a water outlet end of the water pump is communicated with the water storage tank;
   e) a control device disposed in a sealed manner on the support, wherein the camera, the motors and the control device are electrically connected to each other;
   f) a telecontrol device electrically connected to the control device, wherein a remote control device is placed on a lock gate bank when a damage detection is performed on the lock gate sill; and
   g) a display device electrically connected to the control device, wherein the display device is placed on the lock gate bank when a damage detection is performed on the lock gate sill;
   wherein said damage detection apparatus is placed underwater and on an upper surface of the lock gate sill for detecting a damage of the lock gate sill by manipulating a button of the telecontrol device leading to the control device to start the motors, the water pump, and the camera; and
   wherein pictures taken by the camera are transmitted to the display device in time and the damage of the lock gate sill is detected in an intuitive manner in view of the pictures.

2. The damage detection apparatus for a lock gate sill according to claim 1, wherein the filter device comprises a first hopper and a support element disposed in the water inlet barrel and fixedly connected to an inner wall of the water inlet barrel, wherein a bottom of the first hopper is connected to the support element, wherein the first hopper is coaxially disposed with the water inlet barrel, wherein an upper edge of the first hopper is hermetically connected to the inner wall of the water inlet barrel, wherein several filter holes are set on the first hopper, and wherein a neck of the first hopper is communicated with the sediment discharge pipe.

3. The damage detection apparatus for a lock gate sill according to claim 2, wherein a lower part of the first hopper is rotatably connected to the support element by a bearing, wherein the upper edge of the first hopper is hermetically and movably connected to the inner wall of the water inlet barrel, wherein multiple baffle plates are disposed on an inner wall of the first hopper, wherein water inlet passages in the upper end of the water inlet barrel are obliquely provided, and wherein water flows rush into the water inlet barrel from the oblique water inlet passages and impact on the baffle plates, thereby driving the first hopper to rotate.

4. The damage detection apparatus for a lock gate sill according to claim 3, wherein the baffle plates are evenly distributed on the inner wall of the first hopper and are all obliquely disposed in a clockwise or an anticlockwise direction, a tilt direction of the baffle plates being opposite to that of the water inlet passages.

5. The damage detection apparatus for a lock gate sill according to claim 4 comprising two water inlet passages radially disposed, wherein the tilt direction of each of the two water inlet passages is the same.

6. The damage detection apparatus for a lock gate sill according to claim 2, wherein the filter device further comprises a second hopper located below the first hopper and a connecting element disposed on the second hopper, wherein the second hopper is fixed to the neck of the first hopper by the connecting element, wherein the second hopper is coaxially disposed with the first hopper, wherein the neck of the second hopper is fixed to an inner ring of a bearing and is communicated with the sediment discharge pipe, wherein an inner diameter of the neck of the second hopper is larger than an outer diameter of the neck of the first hopper, wherein the neck of the first hopper is inserted in the neck of the second hopper, and wherein several filter holes are set on the second hopper, and the size of the filter holes is smaller than that of the first hopper.

7. The damage detection apparatus for a lock gate sill according to claim 1, wherein four rollers are disposed at the lower part of the support and are respectively driven by four motors.

8. The damage detection apparatus for a lock gate sill according to claim 7, wherein the four rollers are evenly divided into two sets, wherein gears are disposed on each roller, and a track is sleeved on each set of two rollers.

9. The damage detection apparatus for a lock gate sill according to claim 1, wherein an outlet position of the sediment discharge pipe is opposite to a forward direction of the damage detection apparatus for the lock gate sill.

10. The damage detection apparatus for a lock gate sill according to claim 1, wherein an arc-shaped plate is disposed at a front end of the water storage tank, and wherein the arc-shaped plate is in a bow shape for reducing the water resistance when the damage detection apparatus for the lock gate sill moves forward.

11. The damage detection apparatus for a lock gate sill according to claim 1, wherein the water storage tank has a regular octagonal prism structure, and wherein the water inlet barrel is cylindrical, the water storage tank is coaxially disposed with the water inlet barrel.

12. The damage detection apparatus for a lock gate sill according to claim 1, further comprising a battery pack disposed on the support for supplying power to the control module, the motors and the camera.

13. The damage detection apparatus for a lock gate sill according to claim 1, wherein the display device is connected to the control device by a cable.

14. The damage detection apparatus for a lock gate sill according to claim 1, wherein the display device communicates with the control device by a wireless communication module.

15. The damage detection apparatus for a lock gate sill according to claim 1, further comprising a withdrawal rope, wherein the withdrawal rope is tied on the damage detection apparatus for the lock gate sill, and wherein one end of the rope is placed on the lock gate bank when damage detection is performed on the lock gate sill.

* * * * *